(12) United States Patent
Ellson

(10) Patent No.: US 8,534,114 B2
(45) Date of Patent: Sep. 17, 2013

(54) SAND DETECTOR CALIBRATION

(75) Inventor: Nicholas Josep Ellson, Bristol (GB)

(73) Assignee: Vetco Gray Controls Limited, Nailsea (GB)

( * ) Notice: Subject to any disclaimer, the term of this patent is extended or adjusted under 35 U.S.C. 154(b) by 142 days.

(21) Appl. No.: 13/279,539

(22) Filed: Oct. 24, 2011

(65) Prior Publication Data
US 2012/0096922 A1  Apr. 26, 2012

(30) Foreign Application Priority Data

Oct. 25, 2010  (EP) ..................................... 10188689

(51) Int. Cl.
*G01N 33/00* (2006.01)
(52) U.S. Cl.
USPC ........................................... 73/1.82; 73/61.75
(58) Field of Classification Search
None
See application file for complete search history.

(56) References Cited

U.S. PATENT DOCUMENTS

| | | | |
|---|---|---|---|
| 4,056,971 A | 11/1977 | Van Valkenburg | |
| 4,240,287 A * | 12/1980 | Mast et al. | 73/61.75 |
| 4,674,337 A * | 6/1987 | Jonas | 73/861.73 |
| 7,878,047 B2 * | 2/2011 | Hemblade | 73/61.75 |
| 2008/0282781 A1 | 11/2008 | Hemblade | |

FOREIGN PATENT DOCUMENTS

| | | |
|---|---|---|
| JP | 61014570 A | 1/1986 |
| WO | 2010094809 A1 | 8/2011 |

OTHER PUBLICATIONS

EP Search Report issued on Mar. 9, 2011 in connection with EP Application 10188689.

* cited by examiner

*Primary Examiner* — Robert R Raevis
(74) *Attorney, Agent, or Firm* — Global Patent Operation

(57) ABSTRACT

A method of operating an acoustic sand detector deployed at a flowline within a flow system, the detector comprising an acoustic sensor and functioning to produce electrical output signals in dependence on acoustic signals detected by the acoustic sensor, the acoustic signals being at least partially produced by the impact of sand particles within the flow on an object is provided. The method comprises estimating the location of particle impacts on the flowline; and weighting the output signals according to the distance between the estimated location and the detector location.

13 Claims, 1 Drawing Sheet

SAND DETECTOR CALIBRATION

BACKGROUND OF THE INVENTION

1. Field of the Invention

Embodiments of the present invention relate to methods of operating and calibrating acoustic sand detectors, and a method of determining the life expectancy of a flowline. Embodiments of the present invention are particularly suitable for implementation with production flowlines of hydrocarbon wells, for example subsea hydrocarbon production wells.

2. Description of the Prior Art

Production fluid from fluid extraction wells, for example underwater hydrocarbon extraction wells, typically have solid particles such as sand entrained within it. The impact of these particles on the walls of production fluid flowlines, which carry the fluid to the surface, is known to erode the walls. If this erosion is unchecked, the flowline may fail, and leak production fluid to the surrounding region.

The level of erosion will be dependent on various factors, with the most important being the quantity of sand entrained within the fluid. It is therefore desirable to be able to monitor the level of sand within the fluid, to estimate the erosion of the flowline.

To this end, acoustic sand detectors have been commonly used to detect sand, by listening to the impact of the particles on the pipe wall. However, the output of such detectors does not give a clear indication of the levels of sand within the flow, since not all the sand will create a detectable impact in the vicinity of the detector. It is therefore desirable to provide effective calibration of these detectors. However, proper calibration by the manufacturers is difficult due to a number of factors, for example: different types of sand, e.g. with differing grain sizes or density; different environments, e.g. pipe differences leading to differing levels of acoustic signal damping, or internal fluid differences, or background noise; and imprecise knowledge of the exact location where sand hits the wall, e.g. due to flow properties and sand type.

In addition, the above variables may not only be hard to predict, but may also change substantially over the life of a production field, making the measurement from the detectors even more inaccurate.

It is an aim of the embodiments of the present invention to overcome these problems. This aim is achieved by improving the operation and calibration of acoustic sand detectors using local flow characteristics.

BRIEF SUMMARY OF THE INVENTION

Embodiments of the present invention use methodology that can enable more accurate detetmination of sand amounts in flowlines, e.g. production flowlines of a fluid extraction well, and the resulting erosion of equipment.

In accordance with an embodiment of the present invention there is provided a method of operating an acoustic sand detector deployed at a flowline within a flow system, the detector comprising an acoustic sensor and functioning to produce electrical output signals in dependence on acoustic signals detected by the acoustic sensor, the acoustic signals being at least partially produced by the impact of sand particles within the flow on an object. The method comprises estimating the location of particle impacts on the flowline; and weighting the output signals according to the distance between the estimated location and the detector location.

In accordance with another embodiment of the present invention there is provided a method of calibrating an acoustic sand detector deployed at a flowline within a flow system, the detector comprising an acoustic sensor and functioning to produce electrical output signals in dependence on acoustic signals detected by the acoustic sensor, the acoustic signals being at least partially produced by the impact of sand particles within the flow on an object. The method comprises: estimating the location of particle impacts on the flowline; weighting the output signals according to the distance between the estimated location and the detector location; measuring the amount of sand collected at a location downstream of the detector within a certain time period; calculating the amount of the collected sand which has been carried along the flowline based on both the amount of sand collected at a the location downstream of the detector within the time period and the weighted output signals over the time period; and calibrating the detector by integrating the weighted output signals over the period of time.

In accordance with another embodiment of the present invention there is provided a method of determining a life expectancy of a flowline. The method comprises: calibrating an acoustic sand detector deployed at the flowline within a flow system, the detector comprising an acoustic sensor and functioning to produce electrical output signals in dependence on acoustic signals detected by the acoustic sensor, the acoustic signals being at least partially produced by the impact of sand particles within the flow on an object, wherein calibrating the acoustic sand detector comprises: estimating the location of particle impacts on the flowline; weighting the output signals according to the distance between the estimated location and the detector location; measuring the amount of sand collected at a location downstream of the detector within a certain time period; calculating the amount of the collected sand which has been carried along the flowline based on both the amount of sand collected at a location downstream of the detector within the time period and the weighted output signals over the time period; and calibrating the detector by integrating the weighted output signals over the period of time. The method further comprises: measuring the amount of sand passing through the flowline over the period of time using the acoustic sand detector; determining the level of erosion at an area of the flowline; correlating the level of erosion with the measured sand amount to determine a relationship therebetween; and applying the relationship to the output of the acoustic sand detector.

Embodiments of the present invention provide various advantages, including more accurate quantification of sand quantity through the flowline. This in turn can be used to indicate formation damage and possible impending flowline collapse, and accurate determination of erosion. Embodiments of the present invention also provide for updatable or near real-time adjustment of calibration.

Using the above information, well operators are better placed to change operational parameters to increase the life of equipment and/or the hydrocarbon reservoir.

BRIEF DESCRIPTION OF THE SEVERAL VIEWS OF THE DRAWINGS

Embodiments of the present invention will now be described with reference to the accompanying drawings, in which.

DETAILED DESCRIPTION OF THE INVENTION

Figure 1:
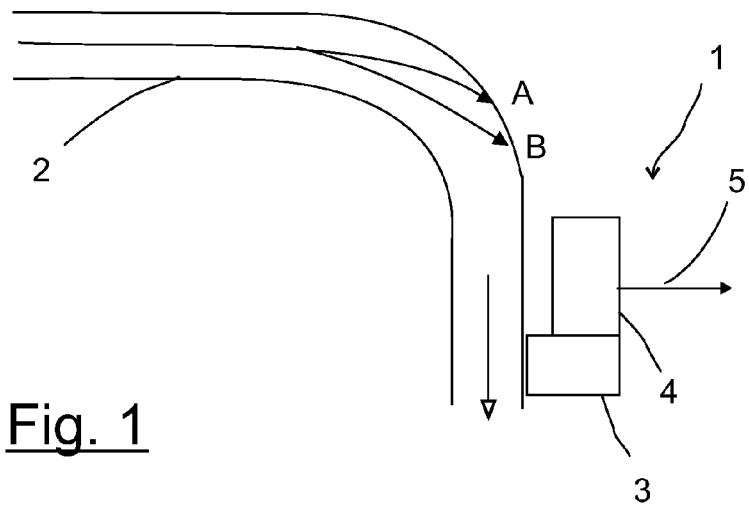
FIG. 1 schematically shows an acoustic sand detector deployed at a flowline, suitable for calibration in accordance with embodiments of the present invention.

FIG. 1 schematically shows an acoustic sand detector 1 deployed at a flowline 2, wherein the fluid flow direction is from the leftmost end to the lower right end as shown by the arrow. The acoustic sand detector 1 comprises an acoustic sensor 3, which picks up acoustic signals, and transducer 4. The acoustic signals received by sensor 3 are fed to the transducer 4, which converts the acoustic signals into electrical output signals 5. Such acoustic sand detectors 1 are known in the art.

FIG. 1 also shows possible flow paths for two sand particles A and B, which as a result of the complex fluid flow within flowline 2 are caused to impact on the side of the flowline 2. As shown, the flowline includes an elbow, and the impacts are likely to occur in the vicinity of the elbow as shown. Assuming that the particles A and B are of similar constitution, mass and speed at the time of impact with the side of the flowline 2, it is apparent that the impact of particle B will cause a greater acoustic signal to be picked up by sensor 3 than the impact of particle A, since the sensor 3 is closer to the impact site of particle B than the impact site of particle A.

Figure 2:
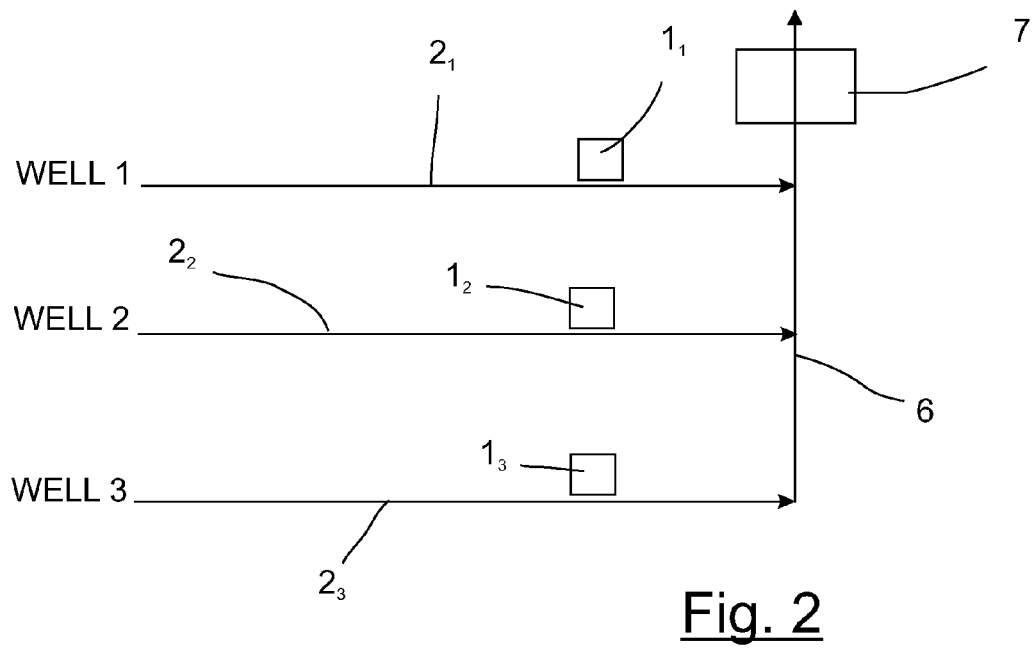
FIG. 2 schematically shows a well system including a number of flowlines fitted with acoustic sand detectors suitable for calibration in accordance with embodiments of the present invention.

FIG. 2 schematically shows an underwater, e.g. subsea, well flow system including a number of flowlines 2 with respective acoustic sand detectors 1 deployed thereat. As shown in FIG. 2, there are three flowlines $2_1$, $2_2$ and $2_3$, equipped with detectors $1_1$, $1_2$ and $1_3$ respectively. Each flowline 2 carries production fluid from a respective well via its "tree" and a production choke (not shown) to a common production flowline 6, which in turn carries production fluid to the surface (not shown). A separator 7 is provided on the common production flowline 6, at a position downstream of all the flowlines 2, which is effective to continuously separate the oil, water and gas. The solids (sand) also drop out and are collected periodically. It should be noted that FIG. 2 is schematic only, and the relative positions of the wells, detectors and sand separator are not to scale.

A method in accordance with embodiments of the present invention, enabling improved operation and calibration of the, or each, sand detector, will now be described.

As mentioned above, the acoustic signal measured by each sand detector 1 will be dependent on: i) the proximity of an impact to the sensor, such that, as shown in FIG. 1, an impact at location B will tend to produce a larger acoustic signal than an impact at location A; ii) the quantity of sand impacting; iii) the velocity of the sand at impact; iv) the size of sand particles impacting; and v) the density of the sand particles impacting.

It is clear that with a single acoustic measurement, but five unknowns, the matter is 'under-determined', i.e. there is more than one possible solution to the equation that relates all of the six variables.

In addition, some of these variables are inter-related, for example, the location of impact will vary with flow velocity and particle properties (size and density), as may the quantity of sand impacting.

Particle properties, including the size and density, can be assessed for example by collecting samples, such as at the separator 7. In most cases it is reasonably safe to assume that these particle properties remain substantially constant, but they could also be updated periodically based on sand collected at the surface.

Using these determined parameters, it is possible to correlate the average impact location of particles within a flowline to the flow velocity.

This correlation can be achieved by using offline techniques such as computational fluid dynamics (CFD) (specifically particle tracking methods within the more general CFD), thus predicting where the particles impact on the flowline wall for given velocities.

The next stage is to determine a value for the flow velocity.

Some more advanced sand detectors use Doppler method to determine the velocity of the particles to increase the accuracy. At present, only the 'high end' acoustic sensors have this capability. If that data is available then it can be used 'as is', if not, then the velocity may be estimated in various ways, e.g.: calculating the bulk density of the fluid using measured differential pressures, usually down-hole to the tree. The pressure drop across a known orifice (typically a choke, but could for example be a venturi) would be measured, and then these two bits of information may be used to calculate the bulk flow rate and hence the velocity. This is a well-known technique, typically termed 'virtual metering'; using the output of a dedicated flow meter, which could be single or multi-phase; or making (relatively crude) assumptions about the velocity based on a determined production choke position or pressure drop across the choke.

With any of these methods it would be assumed that the particle velocity would be the same as the fluid velocity, which is considered a reasonable assumption.

The determined flow velocity may then be fed into the CFI) correlation online to estimate the impact location for that velocity.

This means that all of the unknowns i) v) listed above may be deduced, except for ii) the quantity of sand impacting. However, since the acoustic signal is also measured, there is now sufficient information to derive the sand quantity. In other words, the equation relating the variables may now be solved.

This result can then be factored into the detector calculation to improve its accuracy. In other words, the acoustic signals picked up by a detector 1 can be weighted according to the estimated impact location according to the distance between the estimated location and the detector location. The degree of weighting required can be determined experimentally or by model.

Such predictive techniques may be selected for complexity. For example, although it is difficult to measure particle properties in real-time, the fluid flow properties can be so measured, and so the impact location prediction, and thus the detector weighting, can be updated relatively quickly. Simpler alternatives could be to assume that the flow properties are relatively constant. In this case, the prediction will be updated less regularly. In this respect it is noted that in the short term, choke positions could vary by +/−10% just for pressure balancing reasons. In the longer term (e.g. years) the changes may be more dramatic as the reservoir depletes. A 10% change in flow will change the location of impact of particles.

The sand transport time $t_s$, i.e. the time taken for sand to travel from the vicinity of a detector (i.e. a location at which it is possible for the detector to detect an impact involving the sand) to the separator 7, may be estimated. Since a typical installation practice may be to install the sand detectors on or close to the tree (i.e. one per well), in practice $t_s$ will approximate towards the time taken for the sand to travel from a well to the separator 7.

Typically, $t_s$ will be different for each flowline 2.

Again, there are various techniques of differing complexities which can be used to estimate the sand transport time. A simple technique for example could be to assume that the particles are carried along with the fluid flow at the fluid flow speed.

A more accurate method would be to use a model, such as the "OLGA" (oil and gas simulator) model, described for example at:
http://www.ife.no/main_subjects_new/petroleum_research/flowas?set_language=en&cl=en.

It should be noted that in some cases, e.g. where the flow rates and sand production are substantially constant over time, it may not be necessary to estimate $t_s$.

To take a physical sand measurement, sand is collected from sand separator 7. This is then measured to determine a total sand volume for the field collected within a certain time period (i.e. the time since the sand was last collected in this way), noting that, as shown in FIG. 2, the separator 7 is downstream of all the wells in the field system, and cannot discriminate between sources of sand.

Readings from each acoustic detector 1 in the system may be taken. These readings are weighted according to the particle impact location prediction as described above. For the subsequent steps, only those readings which have been taken over a period of time corresponding to that of the physical sand measurements are required.

The weighted readings from each acoustic detector 1 are correlated with a physical sand measurement, using both the time difference estimated in the sand transport time estimation, and the time which has elapsed since the sand was last collected from separator 7. In this way the amount of collected sand which has been carried along the, or each, flowline may be calculated from the weighted output signals and the amount of collected sand.

To understand this process more easily, a simple example is now set out. Suppose the field is as shown in FIG. 2, i.e. it includes three wells, such that the fluid from each is analysed by a separate respective acoustic detector 1, and the flow from each well passes through a separator 7.

As an example, the total sand collected from the separator 7 after a particular time period T could be 6 kg, and it is assumed that separation of sand by separator 7 is perfect. /Here, $T=t_{c2}-t_{c1}$, where $t_{c1}$ and $t_{c2}$ are successive times at which sand is collected from the separator.

Now, when the separator 7 is emptied, it will include a volume of sand which has already passed by a detector 1. Furthermore, additional sand which has passed by detector 1 will be located in the flowline 2 but will not yet have reached separator 7. Therefore, it is preferable not to directly correlate the detector signal over the time period T with the amount of sand collected by separator 7 over the same period, but instead, to take the sand transport time $t_s$, determined in the sand transport time estimation, into account to select the required time period used. On the other hand, if the flow rates and sand production are substantially constant over time, then it may not be necessary to correct for $t_s$.

In detail, the sand collected over time period T should be correlated with the detector readings commencing at a time $t_{c1}-t_s$ and ending at a time $t_{c2}-t_s$.

The average weighted reading over the relevant time period from each detector is measured, and a simple relationship between the readings from each detector is calculated to enable the proportion of sand collected at the separator 7 which has been carried along the flowline to be calculated, for example:

Average weighted signal (i.e. total estimated sand which has passed in time period T taking into account the sand transport time $t_s$, calculated in the sand transport time estimation, as set out above) from Well 1=a Average weighted signal from Well 2=2a Average weighted signal from Well 3=3a where "a" is a parameter in kg.

Here, equating the amount of sand collected at separator 7 with the total amount of sand carried by each flowline over the relevant time period, gives:

The total readings: a+2a+3a=6 kg, therefore a=1 kg.

It is then necessary to calculate the relative amounts of sand carried along each flowline using the relative average acoustic signal output from each detector 1 over the relevant period of time. In the present example:

the total sand which has passed by the detector 1 in time period T of Well 1=a=1 kg;

the total sand which has passed by the detector 1 of Well 2=2a=2 kg; and the total sand which has passed by the detector 1 of Well 3=3a=3 kg.

The reading from the relevant acoustic sand detector 1 may be correlated to the sand amount determined by correlating the weighted readings from each acoustic detector 1 with a physical sand measurement, in order to calibrate the detector 1. This is achieved by integrating the detector's output signal with respect to time, over the period of time commencing at a time $t_{c1}-t_s$ and ending at a time $t_{c2}-t_s$ as described previously.

Once calibration has been effected as set out above, the, or each, sand detector may be used to directly measure sand passage in the respective flowlines.

With each detector calibrated, they may be used to provide additional information on the well system.

For example, it is possible to use the detectors, for example 'intrusive probes' subsea, with other methods on surface (e.g. ultrasonic) or periodic inspection, to assess erosion occurring within the system. In this case, the cumulative amount of sand passing through the flowline over a period of time is measured by the detector. Additionally, the level of erosion at an area of the flowline is determined from readings taken from a flowline wall thickness monitor, which may for example take the form of an intrusive probe. The measured amount of sand may be correlated with the level of erosion to determine a relationship therebetween, for example a rate at which erosion occurs per quantity of sand, for example an 'erosion per kg' value. This in turn enables a prediction of the remaining life expectancy of flowline equipment to be made, based on current or predicted sand production.

Areas of the flowline more at risk of erosion, which are therefore most suitable for having their levels of erosion determined, may be selected using CFD model, as is described in B2009005 NO for example.

It is noted that systems such as that shown in FIG. 2 provide a level of redundancy for the detector equipment. For example, even if the sand detector $1_1$ fails, it is possible to determine the amount of sand being produced by Well 1 by taking the amount of sand collected at separator 7 and substracting the sand measured by detectors $1_2$ and $1_3$ over the collection period.

If more than one detector fails, then additional information is lost, however it is still possible to produce an estimate of the sand produced, using the relationship previously established by correlating the weighted readings from each acoustic detector 1 with a physical sand measurement.

Using the example described above, suppose that detectors $1_1$ and $1_2$ both fail. In this example, the amount of sand collected by separator 7 over a time period T is 12 kg. It is known from the earlier measurement that Well 3 accounts for about half of the produced sand, i.e. about 6kg. Well 2 accounts for about twice as much of the remainder as Well 1, i.e. Well 2 produces about 4 kg, while Well 1 produces about 2 kg.

Of course, this estimation depends on the relative amounts of sand produced by each well remaining substantially constant.

The above-described embodiments are exemplary only, and other possibilities and alternatives within the scope of the invention will be apparent to those skilled in the art.

What is claimed is:

1. A method of operating an acoustic sand detector deployed at a flowline within a flow system, the detector comprising an acoustic sensor and functioning to produce electrical output signals in dependence on acoustic signals detected by the acoustic sensor, the acoustic signals being at least partially produced by the impact of sand particles within the flow on an object, the method comprising:
    estimating the location of particle impacts on the flowline; and
    weighting the output signals according to the distance between the estimated location and the detector location.

2. The method according to claim 1, wherein estimating the location of particle impacts on the flowline comprises determining a value for the flow velocity.

3. The method according to claim 2, wherein determining a value for the flow velocity comprises estimating the velocity of the flow.

4. The method according to claim 2, wherein determining a value for the flow velocity comprises measuring the velocity of the flow.

5. The method according to claim 1, wherein the flow system comprises an underwater hydrocarbon well.

6. A method of calibrating an acoustic sand detector deployed at a flowline within a flow system, the detector comprising an acoustic sensor and functioning to produce electrical output signals in dependence on acoustic signals detected by the acoustic sensor, the acoustic signals being at least partially produced by the impact of sand particles within the flow on an object, the method comprising:
    estimating the location of particle impacts on the flowline;
    weighting the output signals according to the distance between the estimated location and the detector location;
    measuring the amount of sand collected at a location downstream of the detector within a certain time period;
    calculating the amount of the collected sand which has been carried along the flowline based on both the amount of sand collected at a the location downstream of the detector within the time period and the weighted output signals over the time period; and
    calibrating the detector by integrating the weighted output signals over the period of time.

7. The method according to claim 6, further comprising estimating the time taken for sand to travel from the vicinity of the detector to the downstream location, and using this estimated time to select the period of time used in calculating the amount of the collected sand which has been carried along the flowline.

8. The method according to claim 6, wherein the flow system comprises a plurality of flowlines each comprising an acoustic detector deployed thereat.

9. The method according to claim 8, wherein calculating the amount of the collected sand which has been carried along the flowline comprises equating the amount of sand collected at the location downstream of the detector within the time period with the total amount of sand carried by each flowline over the period of time.

10. The method according to claim 9, wherein calculating the amount of the collected sand which has been carried along the flowline further comprises calculating the relative amounts of sand carried along each flowline using the relative average acoustic signal output from each detector over the period of time.

11. A method of determining a life expectancy of a flowline, the method comprising:
    calibrating an acoustic sand detector deployed at the flowline within a flow system, the detector comprising an acoustic sensor and functioning to produce electrical output signals in dependence on acoustic signals detected by the acoustic sensor, the acoustic signals being at least partially produced by the impact of sand particles within the flow on an object, wherein calibrating the acoustic sand detector comprises:
        estimating the location of particle impacts on the flowline;
        weighting the output signals according to the distance between the estimated location and the detector location;
        measuring the amount of sand collected at a location downstream of the detector within a certain time period;
        calculating the amount of the collected sand which has been carried along the flowline based on both the amount of sand collected at a location downstream of the detector within the time period and the weighted output signals over the time period; and
        calibrating the detector by integrating the weighted output signals over the period of time;
    measuring the amount of sand passing through the flowline over the period of time using the acoustic sand detector;
    determining the level of erosion at an area of the flowline;
    correlating the level of erosion with the measured sand amount to determine a relationship therebetween; and
    applying the relationship to the output of the acoustic sand detector.

12. The method according to claim 11, wherein determining the level of erosion at an area of the flowline comprises measuring the thickness of a flowline wall.

13. The method according to claim 11, wherein the location of the area of flowline for which the level of erosion is determined is selected using computational fluid dynamic modeling.

* * * * *